United States Patent [19]

Fishell

[11] Patent Number: 4,653,485
[45] Date of Patent: Mar. 31, 1987

[54] PENILE ERECTION DEVICE STIFFENER CYLINDER AND IMPLANTATION METHOD

[76] Inventor: Robert E. Fishell, 1027 McCeney Ave., Silver Spring, Md. 20901

[21] Appl. No.: 633,203

[22] Filed: Jul. 23, 1984

[51] Int. Cl.$^4$ ............................................. A61F 2/26
[52] U.S. Cl. ..................................................... 128/79
[58] Field of Search .................. 128/79; 3/1; 128/654; 604/164, 170

[56] References Cited

U.S. PATENT DOCUMENTS

| 2,393,003 | 1/1946 | Smith | 604/170 |
| 4,353,360 | 10/1982 | Finney et al. | 128/79 |
| 4,411,260 | 10/1983 | Koss | 128/79 |

Primary Examiner—Robert P. Swiatek
Assistant Examiner—Cary E. Stone
Attorney, Agent, or Firm—Kane, Dalsimer, Kane, Sullivan and Kurucz

[57] ABSTRACT

A penile implant includes a hollow elastomeric internal cylinder that is coaxial with an external cylinder both of which are rounded at the distal end and suitably secured to one another at this location. The space between the cylinders is designed to receive fluid through a laterally extending port for pressurizing the implant to achieve the erectile state. A root section is adapted to be fastened to the proximal end of the outer cylinder.

When it is desired to implant the prosthesis, the root section is disassociated from the coaxial cylinders and a tool, in rod form, is inserted into the internal cylinder for facilitating the placement of the prosthesis into the dilated corpus cavernosum. When the distal end of the prosthesis is properly located, the surgeon holds the distal end of the prosthesis through the wall of the penis and then removes the tool from the internal cylinder. The root section is then fastened to the proximal end of the prosthesis and then inserted into the root portion of the corpus cavernosum.

13 Claims, 7 Drawing Figures

PENILE ERECTION DEVICE STIFFENER CYLINDER AND IMPLANTATION METHOD

FIELD OF THE INVENTION

This invention is generally in the field of inflatable penile erection devices and more specifically represents an improved stiffener cylinder means and an improved method for implanting an inflatable stiffener cylinder into the corpus cavernosum of the penis.

DESCRIPTION OF THE PRIOR ART

For several decades, devices have been invented and implanted in order to provide a penile erection means for men who suffer the affliction of erectile impotence. The most successful of these devices operate by implanting within the corpora cavernosa of the penis one or more (typically two) stiffener cylinders whose rigidity, when inflated with fluid, provides the desired hardness, stiffness, and increased size for the penis that is necessary for sexual intercourse. The earliest of these devices were merely stiff rods (e.g. Barrington, U.S. Pat. No. 4,151,840) which retained their hardness and size at all times.

An improved penile prothesis was developed by Buuck, as described in U.S. Pat. No. 3,954,102, wherein the stiffener cylinders in the corpora cavernosa were inflatable. The Buuck invention allows a normally hard and stiff penis in the erectile state, while furthermore allowing a smaller and softer condition for the flaccid state. Thus the inflatable stiffener cylinder offers a considerably more physiologic (i.e., normal) situation for the man who requires such a prosthesis.

Various techniques have been developed for implanting stiffener cylinder rods into the corpora cavernosa. Typically, special urological forceps or dilators are used for opening the corpus cavernosum for the insertion of such a stiffener cylinder.

A rigid rod penile prothesis has sufficient rigidity of itself to be able to be readily pushed into a corpus cavernosum after a dilating tool has been used. However, the inflatable stiffener cylinders, though more physiologic in their function and therefore very frequently the preferred device, have insufficient stiffness to be placed within the corpus cavernosum without the assistance of some special tool and/or implant method.

One such implant method was to freeze the cylinders to a rigidly frozen state and then push each one of such cylinders into the corpus cavernosum. This, however, had the disadvantage of increased surgical time, and if the procedure was not done quickly enough, the fluid within the cylinder would thaw therefore precluding insertion. Furthermore, freezing could damage the cylinders and its associated fluid tubing and connections.

An improved tool for positioning stiffener cylinders and a method for using that tool was described by Furlow et. al., in U.S. Pat. No. 4,244,370. The Furlow et. al. invention utilizes a special tool which forces a needle through the distal end of the penis (i.e., the glans) in which the needle has attached to it a surgical thread, which thread is attached through a hole at the distal end of the stiffener cylinder as shown in FIG. 5 of the Furlow et. al. patent. The needle can then be pulled through the glans and the thread to which is attached can be used to pull the cylinder distal tip into the distal end of the corpus cavernosum. The thread is then removed from the cylinder leaving the cylinder's distal tip as close to the glans as is necessary for the cylinder to perform its intended purpose. This procedure is repeated once for each of the two cylinders in each of the two corpora cavernosa.

Although the Furlow et. al. invention has solved the problem of inserting a soft inflatable cylinder into the corpus cavernosum, it does have some disadvantages. One obvious disadvantage is that it requires the penetration of the glans by two reasonably large, threaded needles. Thus there are two wounds in the glans that must heal and there is always the possibility of infection at that point. Furthermore, the Furlow device requires a comparatively complex obturator system which takes additional time to use during surgery and is expensive to produce as compared to the comparatively simple insertion tool described herein.

SUMMARY OF THE INVENTION

Accordingly, an object of the present invention is to provide a simplified tool for insertion of a stiffener cylinder into the corpus cavernosum of the penis.

A further object is to provide a specially designed stiffener cylinder that can use the aforementioned tool for simple insertion of the cylinder into the corpus cavernosum.

A still further object is to provide a method of using the aforementioned tool and cylinder in combination to provide the convenient implantation into the corpus cavernosum of an inflatable penile prothesis stiffener cylinder.

Another object is to perform the stiffener implantation into the corpus cavernosum without penetrating the glans one or more times.

Still further, an object of the present invention is to simplify the stiffener cylinder insertion procedure and thus reduce the time and expense of that procedure and to decrease the possibility of infection.

Still further, an object of the present invention is to provide a means for removing the insertion tool without altering the position of the distal tip of the stiffener cylinder within the distal end of the corpus cavernosum.

Briefly, the invention involves the use of a special tool that is inserted within a hollow, elastomer, internal cylinder that is inside and coaxial with an external cylinder for implantation within the corpus cavernosum of the penis. Between the two cylinders is the working fluid that is pressurized to cause the penis to achieve the erectile state and depressurized to achieve the flaccid state. When the tool is inserted into the internal cylinder, it can be used for pushing the stiffener cylinder into the dilated corpus cavernosum. When the distal tip of the stiffener is at the distal end of the corpus cavernosum, the surgeon holds the bulbous distal tip of that cylinder through the body of the penis and then removes the tool from within the internal cylinder. When the tool is removed, additional working fluid is allowed to flow into the space between the internal and external cylinders thus, causing the internal cylinder to collapse. A root section that is typically semi-rigid is then fastened to the proximal end of the stiffener cylinder. The root section is then placed by the surgeon into the dilated root portion of the corpus cavernosum. This procedure is accomplished without the use of an obturator device and without penetrating the glans of the penis.

BRIEF DESCRIPTION OF THE DRAWINGS

FIG. 3 is a perspective view of the special insertion tool for implanting the stiffener cylinder within the corpus cavernosum of the penis.

FIG. 4 is a longitudinal sectional view of the special insertion tool.

FIG. 5 is an enlarged cross-sectional view of the distal tip of the inserting tool.

FIG. 7 is a fragmentary longitudinal sectional view showing the mating of the stiffener cylinder with the root section.

DETAILED DESCRIPTION OF THE INVENTION

Figure 1:
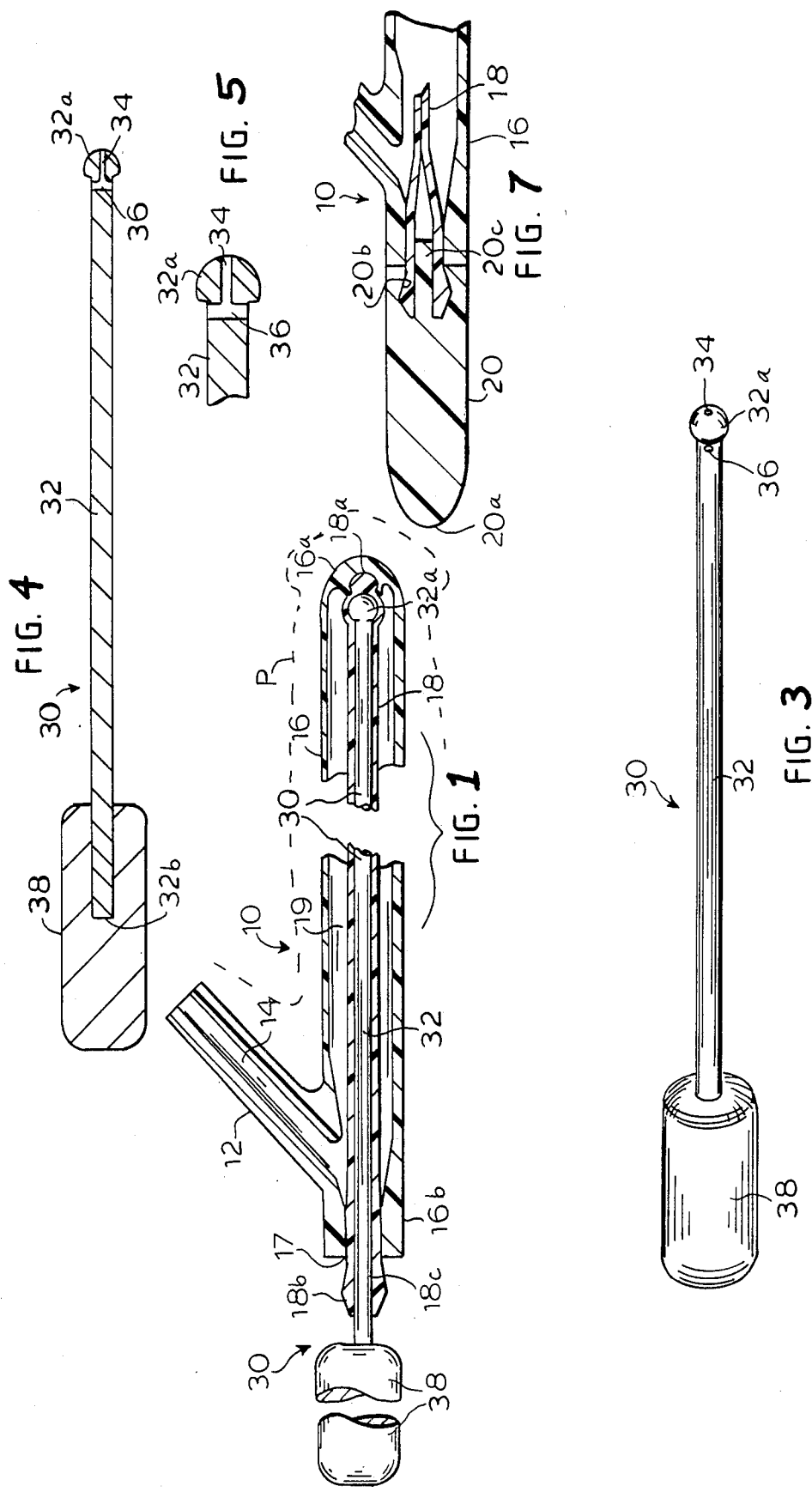
FIG. 1 is a longitudinal sectional view of an inflatable cylinder and insertion tool of this invention.

In the drawing of FIG. 1, improved stiffener cylinder 10 of this invention is shown for use with a penile erection device. The distal portion of the cylinder 10 is implanted within the pendulous portion of the corpus cavernosum of the penis P. A proximal portion of the cylinder 10 resides within the root portion of the corpus cavernosum, i.e., it extends into the body. A connecting section 12 of cylinder 10 has an interior surface 14 that is connected to some source of working fluid such as a resevoir filled with saline solution. When the working fluid enters under pressure into the connection 12 it passes into the root portion of the external cylinder 16 and then into the pendulous portion of the external cylinder causing the penis P to assume its erectile state. When the fluid is removed, the penis P will return to its flaccid state. The working fluid is contained within a chamber 19 that is bounded on its exterior by the external cylinder 16 and on its interior by the internal cylinder 18. Thus when the chamber 19 is pressurized, the erectile state is obtained; and when the fluid is removed from the chamber 19, the flaccid state is obtained.

The external cylinder 16 has thickened tip 16a, and the internal cylinder 18 has thickened tip 18a which are joined together by an adhesive. The external cylinder 16 also has a thicker section 16b at its proximal end (to the left in FIG. 1) and the internal cylinder 18 has thickened proximal end 18b. At its proximal end, the interior surface of the external cylinder 16 is joined with adhesive to the external surface of the proximal end of the interior cylinder 16, this providing a sealed joint 17.

Figure 6:
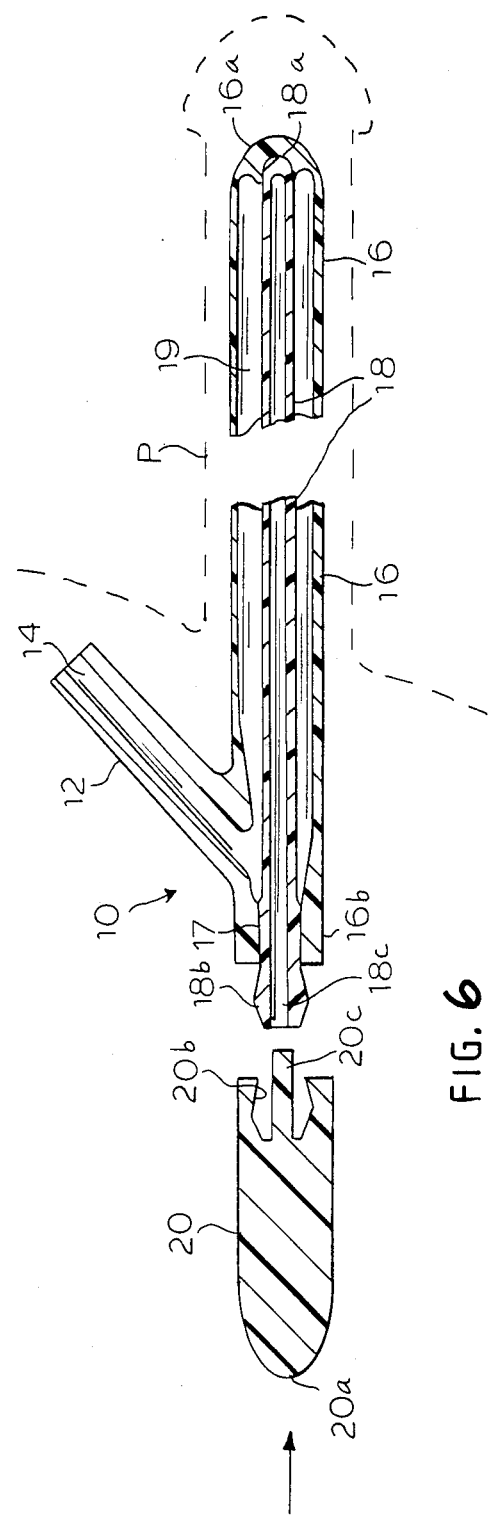
FIG. 6 is an exploded longitudinal sectional view of the implanted inflatable stiffener cylinder.

The distal end of a semi-rigid root section 20 having distal tip 20a (seen to the left in FIG. 6) is designated to mate with the proximal ends of the external cylinder 16 and the internal cylinder 18. Thus, the interior surface 20b of the root 20 will join with the exterior surface of the thickened portion 18b of the internal cylinder 18, and the projection 20c of the root 20 will mate with the interior surface 18c of the proximal end 18b of the internal cylinder 18. This mating is accomplished after the insertion tool 30 (shown in FIGS. 1, 2, 3 and 4) has been used to place the stiffener cylinder into the corpus cavernosum and then has been removed. An elastomer adhesive is used to secure the joining of the root 20 to the stiffener cylinder 10. A preferred adhesive would be Type A silicone adhesive which is frequently used during surgical procedures that require the joining of elastomer parts.

FIG. 7 shows the mating of the cylinder 10 and the root section 20. The material for all of these parts is typically silicone rubber or polyurethane or a similar elastomer. Silicone adhesive is typically used to seal the external cylinder 16 at its proximal and distal ends to the internal cylinder 18, and also to permanently join the root section 20 to the stiffener cylinder 10 which mating is shown in FIG. 7.

FIGS. 3 and 4 show the insertion tool 30 which has a shaft 32, an end ball 32a, and a proximal portion 32b, that is brazed into a handle 38. This tool might typically be fabricated from surgical steel with a ¼ inch diameter shaft 10 inches long and a ⅜ inch diameter handle that is 4 inches long. At the end of the shaft 32 are two holes, an axial hole 34 and a connecting transverse hole 36. FIG. 5 is an enlarged, cross-sectional view of the distal end of the shaft 32 and the end ball 32a. The purpose of the holes 34 and 36 is to allow air to enter the internal cylinder 18 when the tool 30 is withdrawn thus preventing a vacuum condition from being created within the internal cylinder 18.

Figure 2:
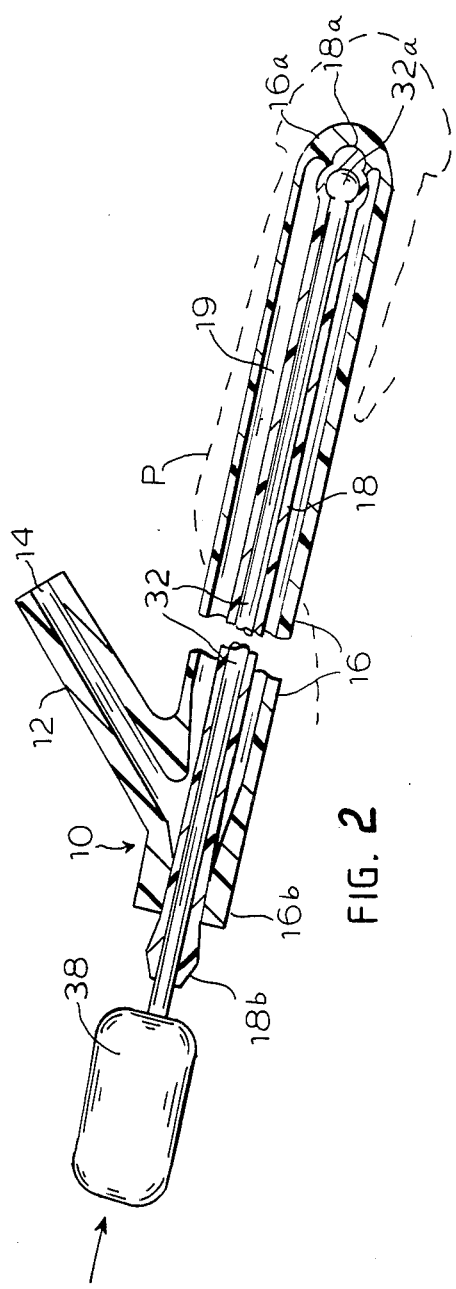
FIG. 2 is an elevational view of the inflatable stiffener cylinder of this invention in the process of being inserted into the corpus cavernosum of the penis utilizing the insertion tool and implantation technique of this invention.

To insert the stiffener cylinder 10 into the corpus cavernosum, the surgeon first makes an incision into the abdomen, and from there accesses the corpus cavernosum in the region where the pendulous portion of the corpus cavernosum joins the root portion. The surgeon then uses dilators to clear out a region within the pendulous portion and the root portion of the corpus cavernosum. The surgeon then inserts the tool 30 into the interior surface 18c of the internal cylinder 18. The combination of the tool 30 and cylinder 10 are then pushed into the pendulous section of corpus cavernosum until the thickened tip 16a of the external cylinder 16 is pushed to the extreme distal end of the corpus cavernosum within the pendulous portion of the penis P as shown in FIGS. 1 and 2. The surgeon will then place the fingers of one hand around the penis at its tip so as to obtain a secure hold on the tool 30 from within the internal cylinder 18. As the tool 30 is slowly withdrawn, the holes 34 and 36 (of FIGS. 5 and 4) allow air to pass into the interior of the internal cylinder 18 so that a vacuum is not developed as the tool is extracted.

When the tool 30 is fully withdrawn, the surgeon will cause fluid to enter into the chamber 19 so as to collapse most of the internal cylinder 18 except for its most proximal portion. This partial collapse of the internal cylinder 18 is shown in FIG. 7. The surgeon will then place adhesive on the distal surfaces of the root 20, and join the root 20 to the stiffener cylinder 10, as shown in FIG. 7. The surgeon will then place the root 20 into the root portion of the corpus cavernosum, and after suturing closed the access cut made into the corpus cavernosum, the surgical implant of the stiffener cylinder 10 and its root section 20 is completed. One should note that the implantation technique has been accomplished with the extremely simple tool without the need for penetrating the glans of the penis with a large needle.

It should be noted here that the root section 20 (as well as the stiffener cylinder) can be made in a variety of lengths and diameters. After measuring the length and diameter of the corpus cavernosum and its root, the surgeon can independently select the best size for the cylinder 10 and the root section 20.

Various other modifications, adaptations and alternative designs are, of course, possible in light of the above teachings. Therefore, it should be understood at this time that within the scope of the appended claims, the invention may be practiced otherwise then as specifically described herein.

What is claimed is:

1. An implantation method for inserting a stiffener cylinder of a penile erection device into the corpus cavernosum comprising:

making an incision in the abdomen for providing access to the corpus cavernosum of the penis in the region where the pendulous portion of the corpus cavernosum joins its root portions;

providing a stiffener cylinder to be implanted with an interiorly extending insert tool; pushing the stiffener cylinder with the interior insert tool into the pendulous section of the corpus cavernosum until the distal end of the stiffener cylinder is at the extreme distal end of the corpus cavernosum within the pendulous portion of the penis; and removing the tool from within the stiffener cylinder.

2. The method in accordance with claim 1 wherein as the tool is removed, securely holding the distal end of the stiffener cylinder through the walls of the penis.

3. The method in accordance with claim 1 wherein the tool is slowly withdrawn from within the stiffener cylinder to prevent the development of suction incident to the withdrawal of the tool.

4. The method in accordance with claim 1 wherein when the tool is fully withdrawn from the stiffener cylinder, securing a root to the stiffener cylinder and placing the root into the root portion of the corpus cavernosum; and closing the access cut made into the corpus cavernosum.

5. An insertion tool for facilitating the insertion of an inflatable stiffener cylinder into the corpus cavernosum of the penis comprising in combination:

a shaft for insertion into an accommodating passage in the inflatable cylinder for supplying a sufficient amount of stiffness to the cylinder for accomplishing the insertion of the cylinder into the corpus cavernosum wherein a suction preventing means at the distal end of the shaft prevents suction conditions from arising at the dital end of the cylinder upon withdrawal of the shaft from the passage.

6. The tool in accordance with claim 5 wherein the suction preventing means includes a ball at the distal end of the shaft which includes holes that permit air to enter the passage of the cylinder incident to withdrawal of the shaft.

7. A stiffener cylinder of a penile erection device for implanting into the corpus cavernosa of the penis comprising in combination:

an external cylinder;

an internal cylinder inside and coaxial with the external cylinder having a coupling means at a proximal end thereof for mating with a root section and having an opening at said proximal end extending internally within the internal cylinder and adapted to receive an insert tool for facilitating the insertion of the stiffener cylinder into the corpus cavernosum of the penis;

the external and internal cylinders defining a chamber for receiving a working fluid that is pressurized to cause the penis to achieve the erectile state and depressurized to achieve the flaccid state.

8. The stiffener cylinder in accordance with claim 7 wherein the distal ends of the external and internal cylinders are closed, thickened and connected with one another.

9. The stiffener cylinder in accordance with claim 7 wherein the proximal ends of the external and internal cylinders are sealed to one another to provide a chamber that is sealed.

10. The stiffener cylinder in accordance with claim 9 wherein coupling means are provided for coupling the chamber with a source of the working fluid.

11. The stiffener cylinder in accordance with claim 9 wherein a root section is connected to the proximal end of the stiffener cylinder.

12. The stiffener cylinder in accordance with claim 9 further comprising a root section connected to the cylinder wherein the connection of the root section and the cylinder includes the coupling means which comprises an extension on the proximal end of the internal cylinder and a mating recess in the root section for receiving the extension.

13. The stiffener cylinder in accordance with claim 7 wherein the coupling means is integral with the internal cylinder.

* * * * *

UNITED STATES PATENT AND TRADEMARK OFFICE
CERTIFICATE OF CORRECTION

PATENT NO. : 4,653,485

DATED : March 31, 1987

INVENTOR(S) : Robert E. Fischell

It is certified that error appears in the above-identified patent and that said Letters Patent is hereby corrected as shown below:

The inventor's name should read --ROBERT E. FISCHELL--

Signed and Sealed this

Eleventh Day of August, 1987

*Attest:*

DONALD J. QUIGG

*Attesting Officer*    *Commissioner of Patents and Trademarks*